US010378951B2

United States Patent
Miklosovic et al.

(10) Patent No.: US 10,378,951 B2
(45) Date of Patent: Aug. 13, 2019

(54) SYSTEM AND METHOD OF INTEGRATED VIBRATION MONITORING IN MOTOR DRIVES

(71) Applicant: Rockwell Automation Technologies, Inc., Mayfield Heights, OH (US)

(72) Inventors: Robert J. Miklosovic, Chardon, OH (US); Mark A. Chaffee, Chagrin Falls, OH (US)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 298 days.

(21) Appl. No.: 15/483,644

(22) Filed: Apr. 10, 2017

(65) Prior Publication Data
US 2018/0292255 A1   Oct. 11, 2018

(51) Int. Cl.
| | |
|---|---|
| *G01H 1/00* | (2006.01) |
| *G01N 29/46* | (2006.01) |
| *G01N 29/14* | (2006.01) |
| *G01N 29/44* | (2006.01) |
| *G01H 3/04* | (2006.01) |
| *G01M 7/00* | (2006.01) |
| *G01M 13/028* | (2019.01) |
| *G01M 13/045* | (2019.01) |
| *H02P 6/10* | (2006.01) |
| *H02P 23/12* | (2006.01) |
| *H02P 23/14* | (2006.01) |

(52) U.S. Cl.
CPC ............ *G01H 1/003* (2013.01); *G01H 3/04* (2013.01); *G01M 7/00* (2013.01); *G01M 13/028* (2013.01); *G01M 13/045* (2013.01); *G01N 29/14* (2013.01); *G01N 29/4436* (2013.01); *G01N 29/46* (2013.01); *H02P 6/10* (2013.01); *H02P 23/12* (2013.01); *H02P 23/14* (2013.01)

(58) Field of Classification Search
CPC .......... G01H 1/003; G01H 3/04; G01M 7/00; G01M 13/028; G01M 13/045; G01N 29/14; G01N 29/4436; G01N 29/46; H02P 6/10; H02P 23/12; H02P 23/14
See application file for complete search history.

(56) References Cited

U.S. PATENT DOCUMENTS

| | | | | |
|---|---|---|---|---|
| 5,541,488 | A * | 7/1996 | Bansal | G01P 3/48 |
| | | | | 318/801 |
| 2017/0080970 | A1* | 3/2017 | Kezobo | B62D 5/0457 |
| 2017/0264231 | A1* | 9/2017 | Kawanishi | G01R 31/44 |
| 2018/0067086 | A1* | 3/2018 | Tian | G01N 29/42 |

* cited by examiner

*Primary Examiner* — David Z Huang
(74) *Attorney, Agent, or Firm* — Boyle Fredrickson, SC

(57) ABSTRACT

An improved system and method for analyzing motor performance to detect vibration of an electric machine controlled by a motor drive is disclosed. A load observer determines an estimated torque present as a load on the motor as a function of input signals corresponding to a desired torque to be generated by the motor and to a measured angular position of the motor during operation. The motor drive determines a frequency response of the estimated torque to identify at what magnitude and frequency any vibration components are present within the estimated torque signal. The motor drive compares the frequency response of the estimated torque signal to set points. If the measured magnitude of vibration at a particular frequency, as seen in the frequency response, exceeds a threshold set in one of the set points for that frequency, the motor drive generates an output signal indicating an excessive vibration is present.

20 Claims, 6 Drawing Sheets

SYSTEM AND METHOD OF INTEGRATED VIBRATION MONITORING IN MOTOR DRIVES

BACKGROUND OF THE INVENTION

The subject matter disclosed herein relates generally to a system and method for monitoring motor vibration in a motor driven mechanical system and, more specifically, to a system and method for using a motor drive to isolate and monitor vibrations present in a motor connected to the motor drive, where the motor is driving the mechanical system.

Electrical rotating machines, such as electric motors or generators, have become widespread and are found in numerous applications and configurations. Electric machines include a stationary component (i.e., the stator) and a rotating component (i.e., the rotor). In electric motors, a magnetic field is established in the rotor, for example via magnets mounted to the rotor or via an electrical current applied to or induced in a coil wound on the rotor. A second, rotating magnetic field is established as a result of the application of a controlled voltage to the stator, and the rotation of the magnetic field in the stator causes the magnetic field in the rotor to rotate, thereby causing rotation of the rotor. A shaft or other drive member is mounted to the rotor and extends outside the rotor housing providing a mechanical coupling to a device, such as a gearbox, pump, or fan that is to be driven as the rotor rotates.

As is known to those skilled in the art, motor drives are utilized to control operation of a motor. Motor drives may be provided to convert input power, from either an alternating current (AC) source or a direct current (DC) source, to the controlled voltage applied to the stator. In certain applications, high performance of the motor and the controlled machine is desired. For example, a servo motor may position a machine tool with high speed and tight position tolerances for repeatable manufacturing of components. The servo motors may be mounted to a machine and coupled, via a gearbox to a drive member, such as ball-screw or rack and pinion used to position one axis of the machine.

Due to the rotational nature of an electric machine, imbalances, for example, on the rotor shaft; misalignments, for example, between the motor shaft and the gearbox; compliant mechanical loads, such as couplings between a motor shaft and a gearbox; or even torque ripple due to machine construction, can result in vibrations or resonance being generated within the control system. These vibrations or resonances may not occur throughout the operating range of the motor but may occur at specific operating frequencies. Such vibrations or resonances may result in increased wear on the motor or require the responsiveness of the motor controller to be reduced to avoid the resonance, resulting in reduced throughput of the controlled machine. Thus, it would be desirable to detect such vibration to provide improved operation of the controlled machine and to extend machine life.

Historically, vibration detection has been performed external to the motor drive, for example, by data acquisition and analysis systems. A vibration sensor may be mounted to the motor and a signal corresponding to vibration is generated and transmitted to the data acquisition and analysis system. Vibration sensors, however, introduce additional expense and configuration requirements. A vibration sensor requires additional clearance for installation and must be aligned such that the transducers within the sensor detect vibration in a desired direction, such as axially or radially with respect to the motor.

As an alternative to a vibration sensor, the motor drive may be configured to transmit data to the data acquisition and analysis system, where the data corresponds to operation of the motor or motor drive. When vibration occurs, the current feedback signal, for example, may include harmonic content at the frequency of vibration. By transmitting such data to the data acquisition and analysis system, the system may analyze the content of the signal and provide a frequency response of the signal which identifies the harmonic content. However, complex control systems, such as a machine tool or a process line include multiple controlled motors or axes of motion. As the number of controlled axes increase, the volume of data being transmitted over a data bus to the data acquisition and analysis system by multiple motor drives similarly increases. In order to detect vibration at a particular frequency, the data must be sampled at a rate at least twice that of the frequency to be detected and preferably the data is sampled at a rate that is an order of magnitude greater than the frequency to be detected. To detect a vibration, for example, at 500 Hz, the data must be sampled at a minimum of one thousand times per second and preferably at five thousand times per second. Each sample for each motor drive must then be transmitted to the data acquisition and analysis system using a significant amount of communications bandwidth both within the motor drive and on an industrial network provided between the data acquisition system and the motor drives.

Thus, it would be desirable to provide an improved system for analyzing motor performance to detect vibration of an electric machine controlled by a motor drive.

BRIEF DESCRIPTION OF THE INVENTION

The subject matter disclosed herein describes an improved system for analyzing motor performance to detect vibration of an electric machine controlled by a motor drive. A load observer executing in the motor drive receives a first input signal, corresponding to a desired torque to be generated by the motor, and a second input signal, corresponding to a measured angular position of the motor during operation. The load observer determines an estimated torque present as a load on the motor shaft as a function of the two input signals. If a vibration is present on the motor shaft, a time varying torque will be present and will be represented in the estimated torque determined by the observer. The motor drive determines a frequency response of the estimated torque to identify at what magnitude and frequency any vibration components are present within the estimated torque signal.

In addition, the motor drive is configured to store one or more set points, where each set point includes a frequency and a magnitude corresponding to the frequency. For each frequency of vibration to be detected, a technician enters a maximum magnitude of vibration for that particular frequency into one of the set points. During operation of the motor drive, the motor drive compares the frequency response of the estimated torque signal to each set point. If the measured magnitude of vibration at a particular frequency, as seen in the frequency response, exceeds the threshold set in one of the set points for that frequency, the motor drive generates an output signal indicating an excessive vibration is present. Further, separate output signals may be generated for each of the set points. The output signals may be connected to a system controller, such as a programmable logic controller which, in turn, may use the signal to generate an alert to an operator of the excessive vibration present on the motor.

According to one embodiment of the invention, a method for monitoring vibration in a motor connected to a motor drive is disclosed. A reference signal is received at a controller in the motor drive, where the reference signal corresponds to a desired operation of the motor connected to the motor drive. A feedback signal is received at the controller from a position feedback device operatively connected to the motor, and a torque reference signal is generated with the controller, where the torque reference signal is a function of the reference signal and of the feedback signal. An estimated torque signal is determined in a condition monitor module executing on the controller, where the estimated torque signal is a function of the feedback signal and of the torque reference signal, and a frequency response of the estimated torque signal is generated with the controller. The frequency response includes multiple frequencies and multiple magnitudes identified within the estimated torque signal, where each magnitude corresponds to one frequency. At least one frequency and at least one threshold is read into the controller from a non-transitory memory device in the motor drive, and each of the thresholds corresponds to one of the frequencies. A status flag on the motor drive is set when the magnitude of the frequency in the frequency response is greater than the threshold of the corresponding frequency stored in the non-transitory memory, and the status flag on the motor drive is reset when the magnitude of the frequency in the frequency response is less than the threshold of the corresponding frequency stored in the non-transitory memory.

According to another embodiment of the invention, a motor drive operative to determine a vibration in a motor connected to the motor drive is disclosed. The motor drive includes a first input, a second input, a non-transitive memory device, and a controller. The first input is configured to receive a reference signal corresponding to a desired operation of the motor connected to the motor drive, and the second input is configured to receive a feedback signal from a position feedback device operatively connected to the motor. The non-transitive memory device is configured to store multiple instructions, and the controller is configured to execute the instructions. The controller generates a torque reference signal as a function of the reference signal and of the feedback signal. The controller determines an estimated torque signal as a function of the feedback signal and of the torque reference signal. The controller generates a frequency response of the estimated torque signal, where the frequency response includes multiple frequencies and magnitudes identified within the estimated torque signal and each magnitude corresponds to one of the frequencies. At least one frequency and at least one threshold is read from the non-transitory memory device, where each of the thresholds corresponds to one of the frequencies. The controller sets a status flag on the motor drive when the magnitude of the frequency in the frequency response is greater than the threshold of the corresponding frequency stored in the non-transitory memory and resets the status flag on the motor drive when the magnitude of the frequency in the frequency response is less than the threshold of the corresponding frequency stored in the non-transitory memory.

According to still another embodiment of the invention, a method for monitoring vibration in a motor connected to a motor drive is disclosed. An estimated torque present at an output of the motor is determined using a controller executing in the motor drive. A frequency response of the estimated torque is generated using the controller executing in the motor drive, where the frequency response includes multiple frequencies and multiple magnitudes identified within the estimated torque and where each magnitude corresponds to one of the frequencies. At least one frequency and at least one threshold is read into the controller from a non-transitory memory device in the motor drive, where each of the thresholds corresponds to one of the frequencies. A status flag on the motor drive is set when the magnitude of the frequency in the frequency response is greater than the threshold of the corresponding frequency stored in the non-transitory memory and reset when the magnitude of the frequency in the frequency response is less than the threshold of the corresponding frequency stored in the non-transitory memory.

These and other advantages and features of the invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Various exemplary embodiments of the subject matter disclosed herein are illustrated in the accompanying drawings in which like reference numerals represent like parts throughout, and in which.

Figure 1:
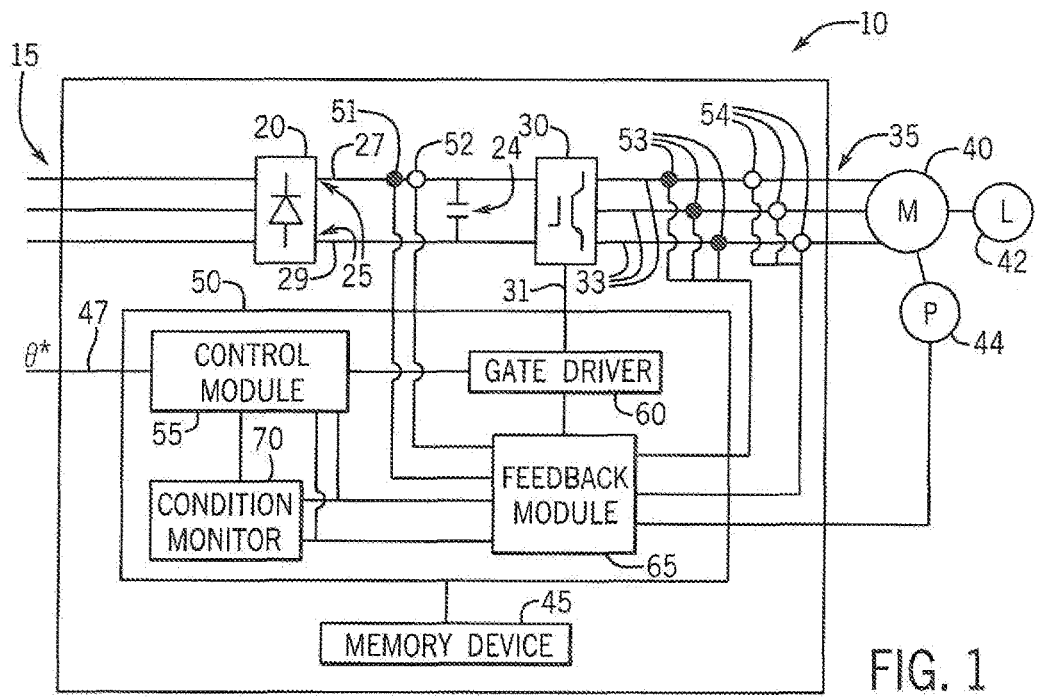
FIG. 1 is a block diagram of a motor drive incorporating one embodiment of the present invention.

In describing the various embodiments of the invention which are illustrated in the drawings, specific terminology will be resorted to for the sake of clarity. However, it is not intended that the invention be limited to the specific terms so selected and it is understood that each specific term includes all technical equivalents which operate in a similar manner to accomplish a similar purpose. For example, the word "connected," "attached," or terms similar thereto are often used. They are not limited to direct connection but include connection through other elements where such connection is recognized as being equivalent by those skilled in the art.

DETAILED DESCRIPTION OF THE PREFERRED EMBODIMENTS

Figure 2:
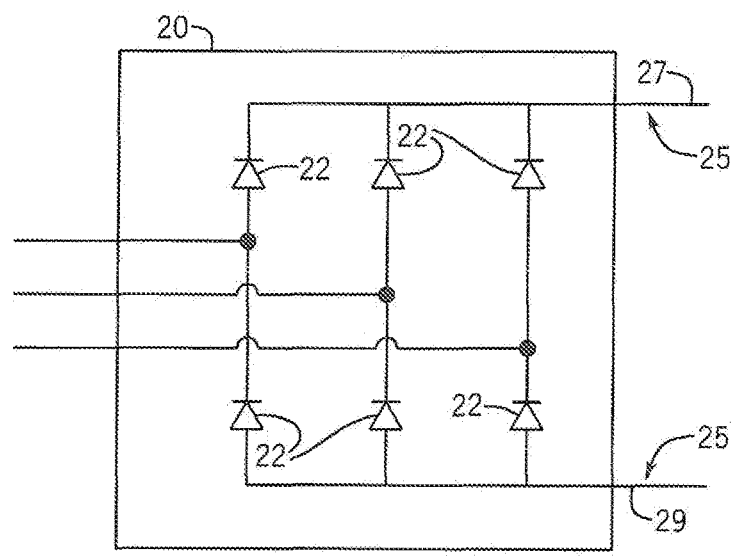
FIG. 2 is a block diagram representation of a rectifier section from the motor drive of FIG. 1.

Turning initially to FIG. 1, a motor drive 10, which may be used in conjunction with the various embodiments of the invention disclosed herein, is configured to receive a three-phase AC voltage at an input 15 of the motor drive 10 which is, in turn, provided to a rectifier section 20 of the motor drive 10. The rectifier section 20 may include any electronic device suitable for passive or active rectification as is understood in the art. With reference also to FIG. 2, the illustrated rectifier section 20 includes a set of diodes 22 forming a diode bridge that rectifies the three-phase AC voltage to a DC voltage on the DC bus 25. Optionally, the rectifier section 20 may include other solid state devices including, but not limited to, thyristors, silicon controlled rectifiers (SCRs), or transistors to convert the input power 15 to a DC voltage for the DC bus 25. The DC voltage is present between a positive rail 27 and a negative rail 29 of the DC bus 25. A DC bus capacitor 24 is connected between the positive and negative rails, 27 and 29, to reduce the magnitude of the ripple voltage resulting from converting the AC voltage to a DC voltage. It is understood that the DC bus capacitor 24 may be a single capacitor or multiple capacitors connected in parallel, in series, or a combination thereof. The magnitude of the DC voltage between the negative and positive rails, 29 and 27, is generally equal to the magnitude of the peak of the AC input voltage.

Figure 3:
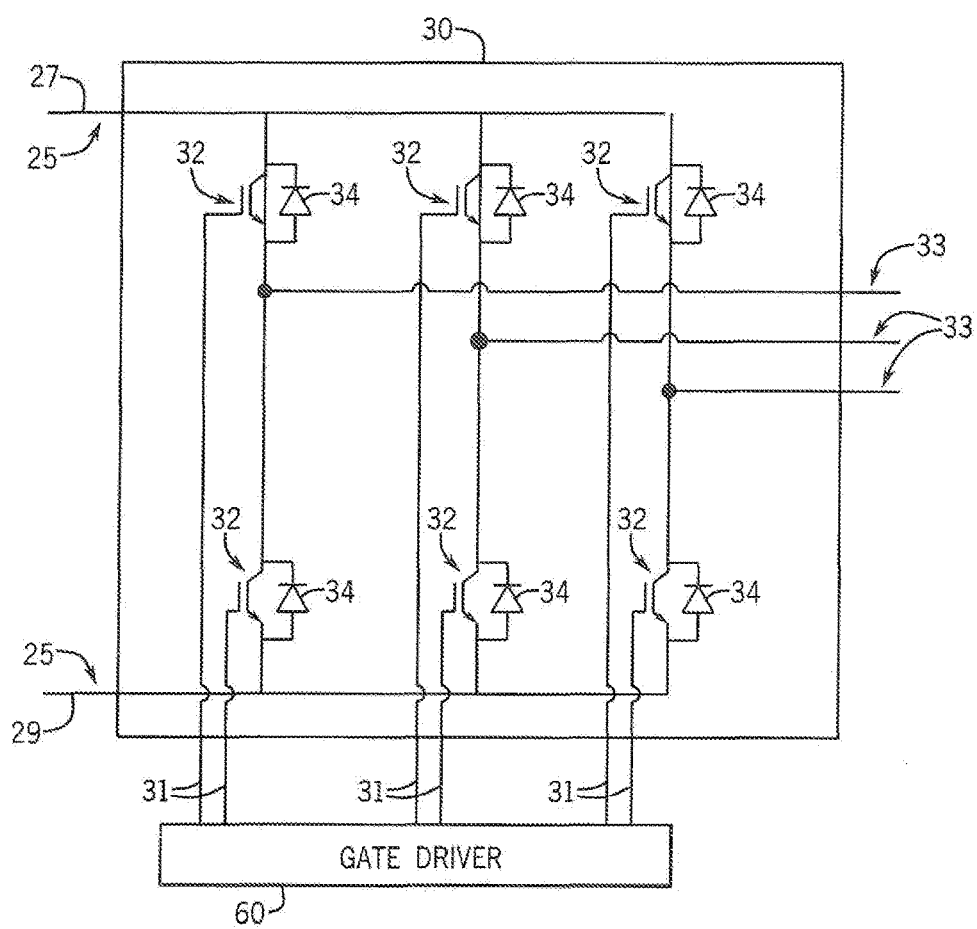
FIG. 3 is a block diagram representation of an inverter section and gate driver module from the motor drive of FIG. 1.

The DC bus 25 is connected in series between the rectifier section 20 and an inverter section 30. Referring also to FIG. 3, the inverter section 30 consists of switching elements, such as transistors, thyristors, or SCRs as is known in the art. The illustrated inverter section 30 includes an insulated gate bipolar transistor (IGBT) 32 and a free-wheeling diode 34 connected in pairs between the positive rail 27 and each phase of the output voltage as well as between the negative rail 29 and each phase of the output voltage. Each of the IGBTs 32 receives gating signals 31 to selectively enable the transistors 32 and to convert the DC voltage from the DC bus 25 into a controlled three phase output voltage to the motor 40. When enabled, each transistor 32 connects the respective rail 27, 29 of the DC bus 25 to an electrical conductor 33 connected between the transistor 32 and the output terminal 35. The electrical conductor 33 is selected according to the application requirements (e.g., the rating of the motor drive 10) and may be, for example, a conductive surface on a circuit board to which the transistors 32 are mounted or a bus bar connected to a terminal from a power module in which the transistors 32 are contained. The output terminals 35 of the motor drive 10 may be connected to the motor 40 via a cable including electrical conductors connected to each of the output terminals 35.

One or more modules are used to control operation of the motor drive 10. According to the embodiment illustrated in FIG. 1, a controller 50 includes the modules and manages execution of the modules. The illustrated embodiment is not intended to be limiting and it is understood that various features of each module discussed below may be executed by another module and/or various combinations of other modules may be included in the controller 50 without deviating from the scope of the invention. The modules may be stored programs executed on one or more processors, logic circuits, or a combination thereof. The controller 50 may be implemented, for example, in a microprocessor, application specific integrated circuit (ASIC), field programmable gate array (FPGA), or other such customizable device. The motor drive 10 also includes a memory device 45 in communication with the controller 50. The memory device 45 may include transitory memory, non-transitory memory or a combination thereof. The memory device 45 may be configured to store data and programs, which include a series of instructions executable by the controller 50. It is contemplated that the memory device 45 may be a single device, multiple devices, or incorporated, for example, as a portion of another device such as an application specific integrated circuit (ASIC). The controller 50 is in communication with the memory 45 to read the instructions and data as required to control operation of the motor drive 10.

The controller 50 receives a reference signal 47 identifying desired operation of the motor 40 connected to the motor drive 10. The reference signal 47 may be, for example, a position reference ($\theta^*$), a speed reference ($\omega^*$), or a torque reference ($T^*$). For a high performance servo control system, the reference signal 47 is commonly a position reference signal ($\theta^*$).

The controller 50 also receives feedback signals indicating the current operation of the motor drive 10. According to the illustrated embodiment, the controller 50 includes a feedback module 65 that may include, but is not limited to, analog to digital (A/D) converters, buffers, amplifiers, and any other components that would be necessary to convert a feedback signal in a first format to a signal in a second format suitable for use by the controller 50 as would be understood in the art The motor drive 10 may include a voltage sensor 51 and/or a current sensor 52 on the DC bus 25 generating a feedback signal corresponding to the magnitude of voltage and/or current present on the DC bus 25. The motor drive 10 may also include one or more voltage sensors 53 and/or current sensors 54 on the output phase(s) of the inverter section 30 generating a feedback signal corresponding to the magnitude of voltage and/or current present on the electrical conductors 33 between the inverter section 30 and the output 35 of the motor drive.

The controller 50 utilizes the feedback signals and the reference signal 47 to control operation of the inverter section 30 to generate an output voltage having a desired magnitude and frequency for the motor 40. The feedback signals are processed by the feedback module 65 and converted, as necessary, to signals for the control module 55. The control module 55 also receives the reference signal 47 and executes responsive to the reference signal 47 and the feedback signals to generate a desired output voltage signal to a gate driver module 60. The gate driver module 60 generates the gating signals 31, for example, by pulse width modulation (PWM) or by other modulation techniques. The gating signals 31 subsequently enable/disable the transistors 32 to provide the desired output voltage to the motor 40, which, in turn, results in the desired operation of the mechanical load 42 coupled to the motor 40.

Figure 4:
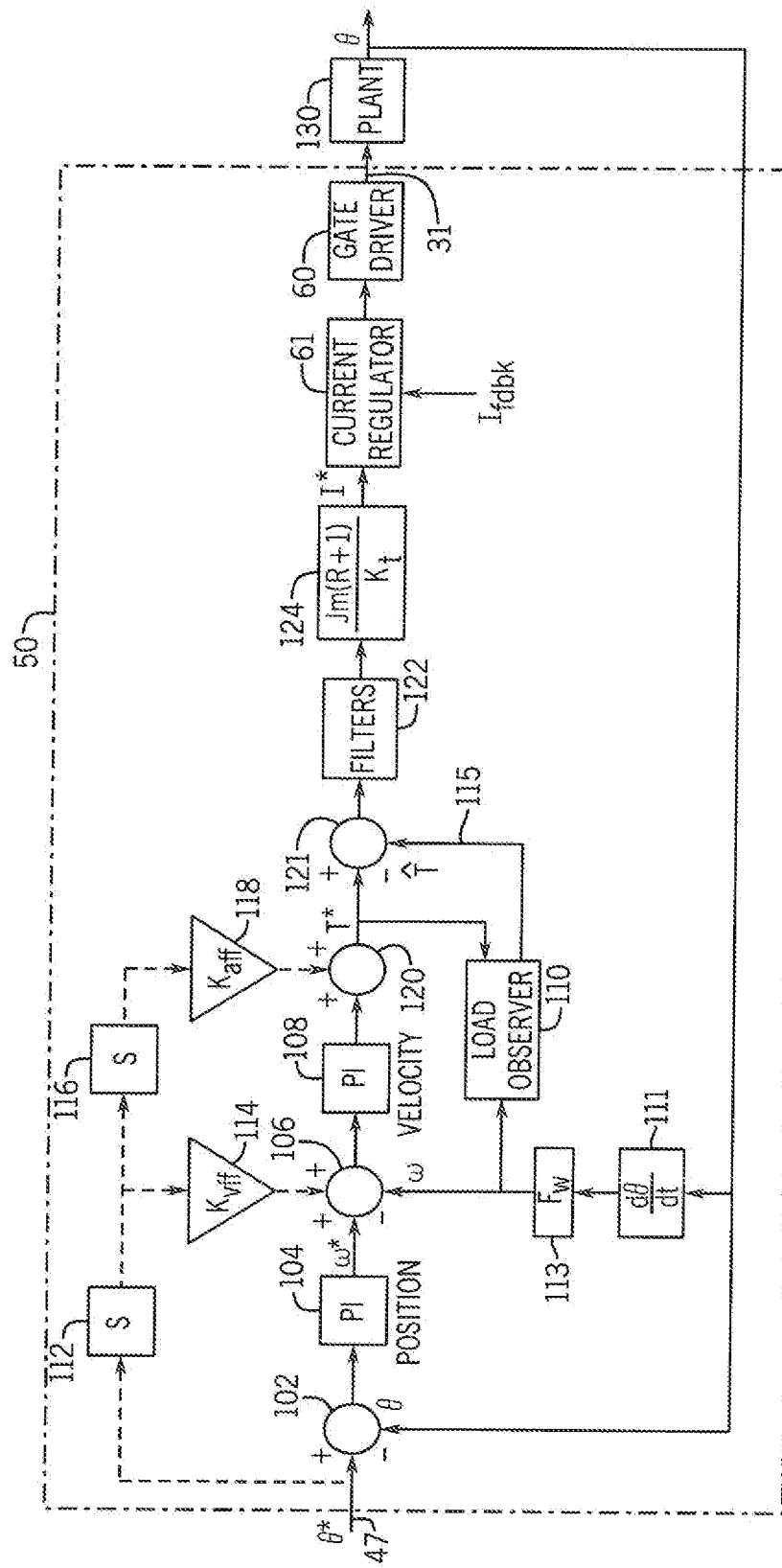
FIG. 4 is a block diagram representation of one embodiment of a controller from the motor drive of FIG. 1.

Referring next to FIG. 4, an exemplary controller 50 for the motor drive 10 is illustrated. The controller 50 receives a position reference signal ($\theta^*$) 47 as an input. As also shown in FIG. 1, the position reference signal ($\theta^*$) 47 is provided to a control module 55. The control module 55 includes a number of control loops. According the embodiment illustrated in FIG. 4, the control module 55 includes a position control loop, a velocity control loop, and a current control loop. The control loops are shown as cascading control loops where an output of one control loop is provided as an input to another control loop. It is contemplated that various other control topologies may be utilized within the motor drive 10.

In the position control loop, the position reference signal ($\theta^*$) 47 is compared to a position feedback signal ($\theta$) at a first summing junction 102. A position error signal is output from the first summing junction 102 and input to a position loop controller 104. According to the illustrated embodiment, the position loop controller 104 is a proportional-integral (PI) controller. Optionally, the position loop controller 104 may be just a proportional (P) controller or further include a derivative (D) component. Each of the proportional (P), integral (I), and/or derivative (D) components of the position loop controller 104 includes a controller gain. The position loop controller gains are commonly referred to as a position loop proportional gain (Kpp), position loop integral gain (Kpi), and a position loop derivative gain (Kpd). The output of the position loop controller 104 is a velocity reference signal (ω*).

In the velocity control loop, the velocity reference signal (ω*) is compared to a velocity feedback signal (ω) at a second summing junction 106. The velocity feedback signal (ω) is generated by taking a derivative, as shown in the derivative block 111, of the position feedback signal (θ). The velocity feedback signal (ω) may also be filtered by a velocity filter block 113. A velocity error signal is output from the second summing junction 106 and input to a velocity loop controller 108. According to the illustrated embodiment, the velocity loop controller 108 is a proportional-integral (PI) controller. Optionally, the velocity loop controller 108 may be just a proportional (P) controller or further include a derivative (D) component. Each of the proportional (P), integral (I), and/or derivative (D) components of the velocity loop controller 108 includes a controller gain. The velocity loop controller gains are commonly referred to as a velocity loop proportional gain (Kvp), velocity loop integral gain (Kvi), and a velocity loop derivative gain (Kvd). The output of the velocity loop controller 108 is an acceleration reference signal.

The control module 55 may also include feed forward branches. According to the illustrated embodiment, the control module 55 includes feed forward branches for both the velocity and the acceleration elements. The position reference signal (θ*) is passed through a first derivative element 112 to obtain a velocity feed forward signal. The velocity feed forward signal is multiplied by a velocity feed forward gain (Kvf) 114 and combined with the velocity reference signal (ω*) and the velocity feedback signal (ω) at the second summing junction 106. The velocity feed forward signal is passed through a second derivative element 116 to obtain an acceleration feed forward signal. The acceleration feed forward signal is multiplied by an acceleration feed forward gain (Kaf) 118 and combined with the acceleration reference signal at a third summing junction 120 to generate a torque reference signal (T*).

Figure 5:
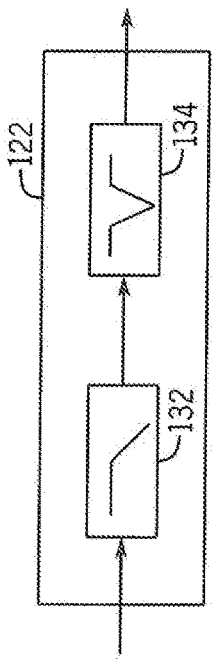
FIG. 5 is a block diagram representation of a filter section from the controller of FIG. 5.

The torque reference signal (T*) output from the third summing junction 120 is further processed prior to generating gate signals 31 for the inverter section 30. The torque reference signal (T*) is provided as an input to a filter section 122 and to a load observer 110. With reference also to FIG. 5, the filter section 122 may include one or more filters to remove unwanted components from the control system, such as a low pass filter 132 to attenuate undesirable high frequency components or a notch filter 134 to attenuate specific frequency components having an undesirable effect on the controlled mechanical load. It is further contemplated that additional filters may be included in the filter section 122 without deviating from the scope of the invention.

The load observer 110 uses the torque reference signal (T*) along with the velocity feedback signal (ω) to generate an estimated value of the load torque. The load observer 110 models the physical system present at the output of the motor but executes with faster dynamics than the physical system to generate an estimate of the load present at the output of the motor. The torque estimate may include both expected components and unexpected, or disturbance, components of loading applied to the motor. According to one embodiment of the invention, the load observer may determine an estimated disturbance torque according to Eq. 1, presented below.

$$\widehat{T}_d = T_{ref} - J\omega \quad (1)$$

where:

$\widehat{T}_d$ = estimated disturbance torque;
Tref = torque reference;
J = inertia; and
ω = angular velocity.

It is understood that the load observer 110 may utilize other methods of estimating the disturbance torque without deviating from the scope of the invention. For example, the load observer 110 may be tunable in a similar manner to the control loops discussed above. The observer may include a proportional (P) branch, an integral (I) branch, and/or a derivative (D) branch. Each branch of the observer includes a proportional (P), integral (I), and/or derivative (D) gain. The observer gains are commonly referred to as an observer proportional gain (Kop), an observer integral gain (Koi), and an observer derivative gain (Kod). The load observer 110 may further include one or more filters to reduce undesirable components from the torque estimate. The load observer may use alternate input signals, such as angular position and angular acceleration either separately from or in combination with the angular velocity to determine the torque estimate. Similarly, the output of the load observer may be an estimated load torque signal, an estimated disturbance torque, or a combination thereof.

The output of the filter section 122 is passed through a torque gain block 124. The torque gain block 124 includes a torque constant (Kt) which defines a relationship between the current provided to the motor 40 and the torque output by the motor. The torque gain block 124 may include one or more additional gain elements combined with the torque constant (Kt) to produce a desired current reference (I*) to a current regulator 61. The current regulator receives a current feedback signal ($I_{fdbk}$) from the current sensors 54 at the output of the motor drive 10 and utilizes a current controller, which may include proportional, integral, and/or derivative components to regulate the current in the motor 40. The output of the current regulator 61 is provided to the gate driver 60 which, in turn, generates the switching signals 31 to the inverter section 30.

The output of the gate driver 60 is illustrated as being supplied to the plant 130 of the controlled system. In a motion control system, the plant 130 typically includes the inverter section 30 of the motor drive 10, the motor 40, a mechanical load 42, a position feedback device 44, and mechanical couplings between the motor 40 and mechanical load 42 or between the motor 40 and a position feedback device 44. The position feedback device 44 generates the position feedback signal (θ) used by the control module 55.

With reference again to FIG. 1, the output of the control module 55 is provided as an input to the gate driver module 60. The gate driver module 60 converts the output of the current regulator to a desired output voltage having a variable amplitude and frequency, where the amplitude and frequency are selected to produce the desired operation of the motor 40. The gate driver module 60 then generates the gating signals 31 used by pulse width modulation (PWM) or by other modulation techniques to control the switching elements in the inverter section 30 to produce the desired output voltage. The gating signals 31 subsequently enable/disable the transistors 32 to provide the desired output voltage to the motor 40, which, in turn, results in the desired operation of the mechanical load 42 coupled to the motor 40.

As discussed above, the control module 55 may include a number of controller gains and filter settings which affect performance of the motor drive 10. The controller gains and filter settings need to be adjusted or tuned in order to achieve a desired performance level. Settings for each of the controller gains and filter settings are stored in a non-volatile portion of the memory device 45 to retain the settings when power is removed from the motor drive 10. Typically, the settings are transferred to a volatile portion of the memory device 45 upon applying power to the motor drive 10 to provide for quick reads of the values for use in execution of the control module 55. Default values for each of the controller gains and filter settings may be stored in the memory device 45 from the factory, where the default settings are typically configured to provide a conservative response of the control module 55, such that the a broad range of applications may be started up with little chance of exciting resonances in the mechanical system or having other undesirable and/or unstable operation of the controlled load.

Figure 6:
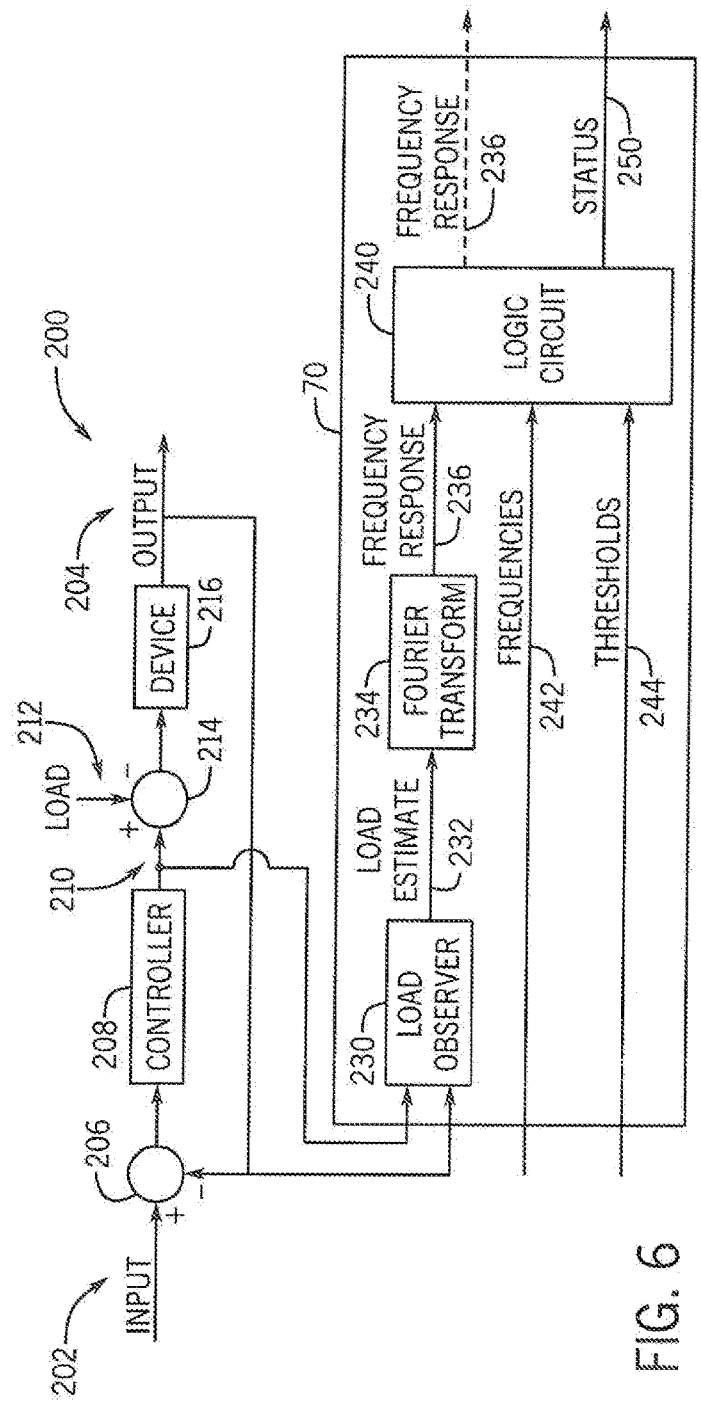
FIG. 6 is a block diagram representation of one embodiment of a system for detecting vibration.

Turning next to FIG. 6, a condition monitor module 70 according to one embodiment of the invention is illustrated. The condition monitor module 70 is illustrated with respect to a general control system 200 having a single input 202 and a single output 204. A first summing junction 206 provides a difference between the input 202 and output 204 as an input to a controller 208. A second summing junction 214 determines a difference between the output 210 of the controller 208 and a feedback signal 212 corresponding to a load on the system. The difference from the second summing junction 214 is provided as an output to a device 216 in the controlled system.

The condition monitor module 70 monitors performance of the device 216 and detects vibrations or oscillations in the device 216 at predefined frequencies. The output 210 of the controller and the output signal 204 of the controlled system 200 are provided as inputs to a load observer 230. The load observer 230 determines an estimate 232 of the load present on the controlled system 200. The load estimate 232 is provided as an input to a transform module 234 that is operative to provide a frequency response 236 of the load estimate 232. According to the illustrated embodiment, the transform module 234 executes a Fourier transform on the load estimate 232 in order to generate the frequency response 236 output. It is contemplated that the Fourier transform may be a standard Fourier transform, fast Fourier transform, or discrete Fourier transform. One embodiment of the Fourier transform will be discussed in more detail below.

The condition monitor module 70 also includes a logic circuit 240 operative to identify vibrations or oscillations in the controlled system 200 that exceed a predefined level. As illustrated, the logic circuit 240 receives the frequency response 236 of the load estimate 232 as an input. The logic circuit also receives at least one frequency 242 and at least one threshold 244 corresponding to the frequency 242 as an input. The logic circuit 240 uses each of the frequencies 242 input to identify the corresponding frequency component within the frequency response 236. The logic circuit 240 then compares the magnitude of the frequency component in the frequency response 236 to the threshold 244 for that frequency and sets a status flag 250 as a function of whether the magnitude of the frequency component exceeds the threshold 244. Optionally, the logic circuit may also provide the frequency response 236 as an output from the condition monitor module 70.

According to another embodiment of the invention, the logic circuit 240 may compare the magnitudes of multiple frequency components in the frequency response to multiple corresponding thresholds. When monitoring the condition of the mechanical system driven by the motor 40, certain conditions may exhibit vibrations at multiple frequencies. The logic circuit may, therefore, set a status flag 250 if the combination of frequencies each exceed the corresponding threshold.

Figure 7:
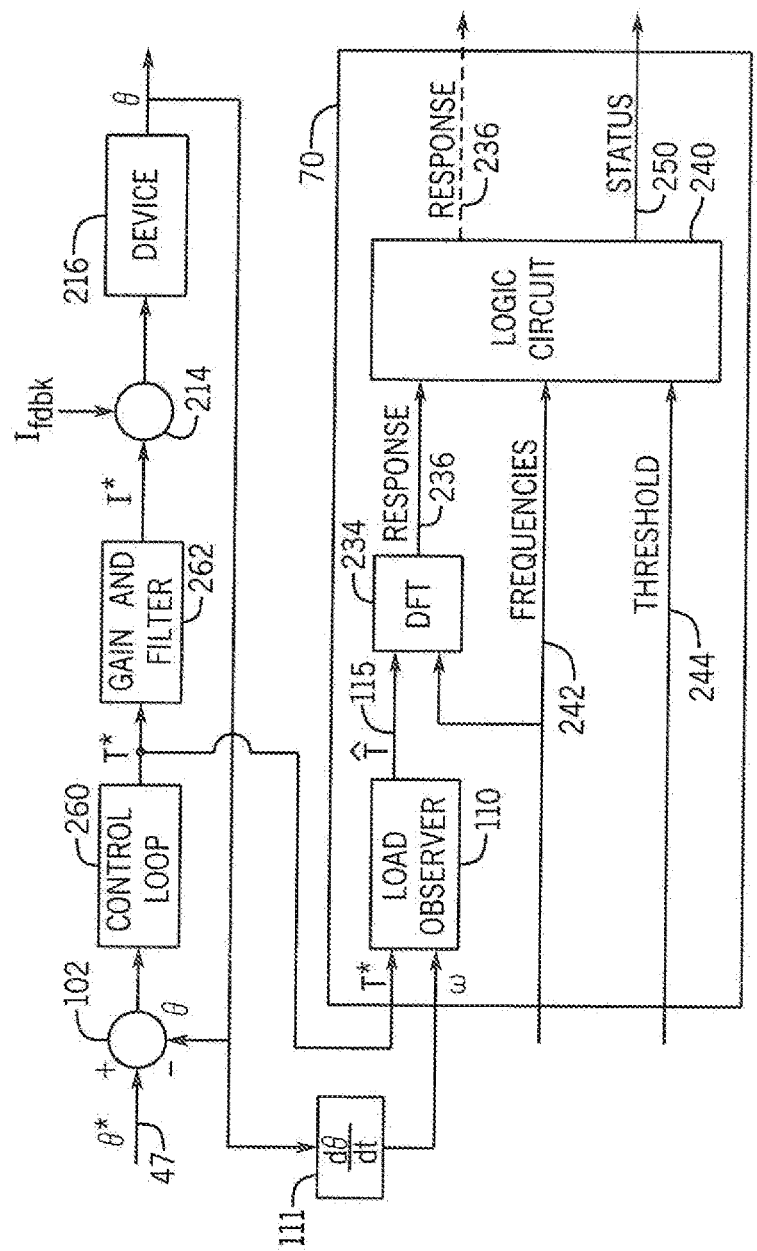
FIG. 7 is a block diagram representation of the system for detecting vibration shown in FIG. 6 as implemented in the motor drive of FIG. 1.

Turning next to FIG. 7, an embodiment of the condition monitor module 70 applied to the motor drive 10 of FIG. 1 is illustrated. The input signal 202 of the general control system 200 corresponds to the position reference ($\theta^*$) signal 47 input to the controller 50 (as shown in FIG. 1). The angular position ($\theta$) is measured by the position feedback device 44 and provided to the first summing junction 102 (as also shown in FIG. 4). A portion of the controller 50 from FIG. 4 is illustrated as the control loop block 260 from which the torque reference signal ($T^*$) is generated. The filter section 122 and torque gain block 124 are combined into the gain and filer block 262 from which the current reference ($I^*$) is output. The current reference ($I^*$) and current feedback signal ($I_{fdbk}$) are provided to summing junction 214 and the output of the summing junction 214 is provided to the device 216. The device 216, as illustrated in FIG. 7, corresponds to the current controller, gate driver 60, and plant 130 of the system show in FIG. 4.

The condition monitor module 70 uses the torque reference signal ($T^*$) and the measured feedback signal from the position feedback device 44 to determine an estimated torque value 115. As illustrated, the measured feedback signal corresponds to an angular position ($\theta$) of the motor 40. The angular position signal is converted to an angular velocity ($\omega$) signal via a derivative block 111 and the angular velocity ($\omega$) is provided as an input to the load observer 110. It is contemplated that the angular position, angular velocity, or angular acceleration, all of which may be determined as a time varying function of the measured feedback signal from the position feedback device 44, may be provided as an input to the load observer 110. As demonstrated above in equation 1, the estimated disturbance torque may be output from the load observer 110, where the disturbance torque corresponds to the unexpected components of torque, such as unexpected vibrations, present at the motor 40. Optionally, an estimated torque value, including expected loading of the motor, may also be output from the load observer 110. The estimated torque signal 115 is provided as an input to a Discrete Fourier Transform (DFT) module 234.

The DFT module 234 performs an enhanced DFT routine to determine the magnitude of vibration present at specific frequencies of interest. Typically, a DFT routine will transform a sampled time signal into a complex vector, containing magnitude and phase information, for a number of evenly spaced frequency bins between zero hertz and the sampling frequency as described in Eq. 2, presented below.

$$X(k)=\Sigma_{n=1}^{N}x(n)e^{-j2\pi(k-1)(n-1)/N} \text{ for } k=1,\ldots,N/2 \qquad (2)$$

where:
X(k)=frequency response at evenly spaced frequency
N=number of samples; and
x(n)=nth sample value.
However, the frequency bins may not correspond directly to the frequency of interest. A resulting measurement error, referred to as spectral leakage, occurs when determining a magnitude of a frequency component present in the input signal that does not directly correspond to one of the frequency bins. Measurement accuracy may be improved by increasing the number of samples; however, the DFT, as shown in Eq. 2, is evaluated as a squared relationship of the number of samples. As a result, the computational requirements increase quickly as the number of samples is increased. To address the computational requirements of the traditional DFT, the DFT module 234 performs an enhanced DFT routine to determine the magnitude of vibration present at specific frequencies of interest.

The DFT module 234, as shown in FIG. 7, performs a DFT only on the frequencies of interest to determine the magnitude of vibration present in the estimated torque signal at those frequencies. The DFT module 234 receives as inputs the frequencies 242 of interest, which are also provided to the logic circuit 240. Rather than determining a frequency response across a uniformly spaced number of frequency bins (as performed by Eq. 2), the enhanced DFT determines a frequency response at the desired frequencies of interest as described in Eq. 3, presented below.

$$X(f) = \sum_{n=1}^{N} x_{nom}(n) e^{-j2\pi f T(n-1)} \quad (3)$$

where:
X(f)=frequency response at desired frequency;
f=desired frequency;
T=sampling frequency,
N=number of samples; and
$x_{nom}$(n)=nth sample value.

The condition monitor module 70 of FIG. 7 also includes the logic circuit 240 operative to identify vibrations or oscillations in the controlled system 200 that exceed a predefined level. As illustrated, the logic circuit 240 receives the frequency response 236 of the load estimate 115 as determined by the enhanced DFT routine as an input. The logic circuit also receives each of the frequencies 242 provided to the DFT module 234 and at least one threshold 244 corresponding to each frequency 242 as an input. The logic circuit 240 uses each of the frequencies 242 input to identify the corresponding frequency component within the frequency response 236. The logic circuit 240 then compares the magnitude of the frequency component in the frequency response 236 to the threshold 244 for that frequency and sets a status flag 250 as a function of whether the magnitude of the frequency component exceeds the threshold 244. Optionally, the logic circuit may also provide the frequency response 236 as an output from the condition monitor module 70.

The logic circuit 240 may be configured to set status flags 250 based on a number of different conditions. Certain conditions present in the mechanical system controlled by the motor 40 will exhibit a vibration at a single frequency. For example, unbalanced forces applied to both sides of a rotating machine will generate a vibration at a single frequency that is approximately equal to one times the rotational speed of the motor 40. Other conditions present in the mechanical system controlled by the motor 40 may exhibit vibrations at multiple frequencies. For example, angular misalignment of shafts may result in vibrations of different magnitudes at three different frequencies. Specifically, a first vibration will be present at about one times the rotational speed of the motor 40, a second vibration will be present at about two times the rotational speed of the motor 40, and a third vibration will be present at about three times the rotational speed of the motor 40. The expected magnitude of vibration at each multiple of the rotational speed is different. The logic circuit 240 may compare the magnitudes of the multiple frequency components in the frequency response to multiple corresponding thresholds, and, if all of the magnitude of all three frequency components exceed the threshold, a status flag 250 indicating angular misalignment may be set.

In operation, the condition monitor module 70 provides a system, integrated within the motor drive 10, which analyzes motor performance to detect vibration of the motor 40 controlled by the motor drive. With reference to the embodiment of the condition monitor module 70 illustrated in FIG. 7, the embodiment of the motor drive 10 illustrated in FIG. 1, and the embodiment of the controller 50 illustrated in FIG. 4, the motor drive 10 receives a position reference (θ*) signal as an input to the controller 50 to indicate desired operation of the motor 40 connected to the motor drive 10. The motor drive 10 executes the control module 55 to provide a variable amplitude and variable frequency voltage to the motor 40 which causes the motor 40 to rotate according to the desired angular position indicated in the position reference (θ*) signal.

The position feedback device 44 generates a signal corresponding to the angular position of the motor 40 and provides the signal to the motor drive 10. As would be understood in the art, the position feedback device 44 generates, for example, a pulse train, multiple pulse trains offset from each other, a sinusoidal signal, or multiple sinusoidal signals offset from each other, where the pulse train or sinusoidal signal corresponds to motion of the motor 40. Still other position feedback devices may generate a serial data stream with a bit pattern or position information. The signal from the position feedback device 44 is provided to the feedback module 65 and converted to a value corresponding to the angular position (θ) of the motor 40. The angular position (θ) of the motor 40 is provided as a feedback signal to the control module 55.

As previously discussed, the controller 50 provides the position reference (θ*) signal and the angular position (θ) feedback signal to the position control loop 104. The output of the position control loop 104 and the angular velocity (ω), determined as a derivative of the angular position (θ) are provided as inputs to the velocity control loop 108. The velocity control loop 108 outputs a torque reference signal (T*).

The condition monitor module 70 uses the torque reference signal (T*) and the angular velocity (ω) feedback signal to determine an estimated torque value. It is noted that the load observer 110 is illustrated as part of the control module in FIG. 4 and as part of the condition monitor module 70 in FIG. 7. As previously indicated, it is contemplated that various functions may be performed by different modules without deviating from the scope of the invention. A single load observer 110 may be utilized for both functions or, optionally, two different load observers 110 may be utilized where each load observer 110 may use either the same or different methods of determining an estimated torque value.

Figure 8:
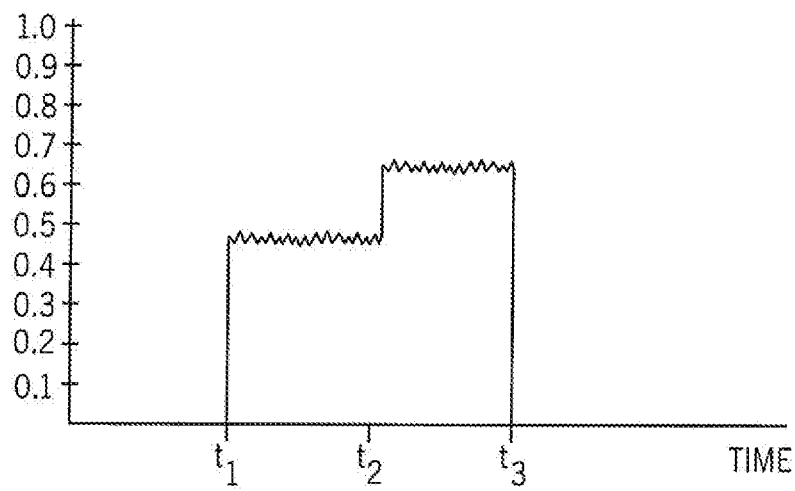
FIG. 8 is a graphical representation of an estimated torque value determined by one embodiment of a condition monitor module utilized by the present invention.

An exemplary estimated torque signal is illustrated in FIG. 8. Initially, the motor 40 is not commanded to run. At time, t1, a first position reference (θ*) signal is received, resulting in the motor 40 operating at a first torque level of about fifty percent of rated torque. A small vibration is observed as a ripple on the estimated torque signal. At time, t2, a second position reference (θ*) signal is received, resulting in the motor 40 operating at a second torque level of about seventy percent of rated torque. A small vibration is still observed as a ripple on the estimated torque signal. Optionally, the estimated torque signal may be a disturbance torque estimate and may include just the ripple torque observed in FIG. 8.

An operator may initially define at least one expected frequency 242 of vibration for which the motor drive 10 is to monitor. The frequency 242 is selected according to an expected frequency of vibration. A number of conditions exist that cause vibration at a known frequency. An unbalanced force exerted on two ends of a rotating machine due, for example, to unbalanced weight, unbalanced coupling, or uneven wear of bearings on either end of the rotating machine can cause a vibration at one times the angular velocity of the rotating machine. Other conditions exist that cause vibration at multiple frequencies. For example, a misalignment in coupling between a motor and the rotating load coupled to the motor may result in vibration at one, two, and three times the angular velocity of the rotating machine. In applications during which the motor 40 is expected to operate at a constant speed for long durations the expected frequency 242 of vibration may be set equal to the constant speed of the motor or to multiples, such as one, two, or three times the constant angular velocity of the motor. In other applications during which the motor 40 may start and stop frequently or operate at varying speeds, the expected frequency 242 of vibration may be set as a multiplier of the angular velocity. In either instance, the expected frequency of vibration is entered into the motor drive 10 and stored in the memory device 45. A threshold 244 value is also entered and stored in the memory device 45 for each expected frequency 242 of vibration. The threshold 244 corresponds to a maximum magnitude of vibration that is acceptable during operation of the motor 40.

Figure 9:
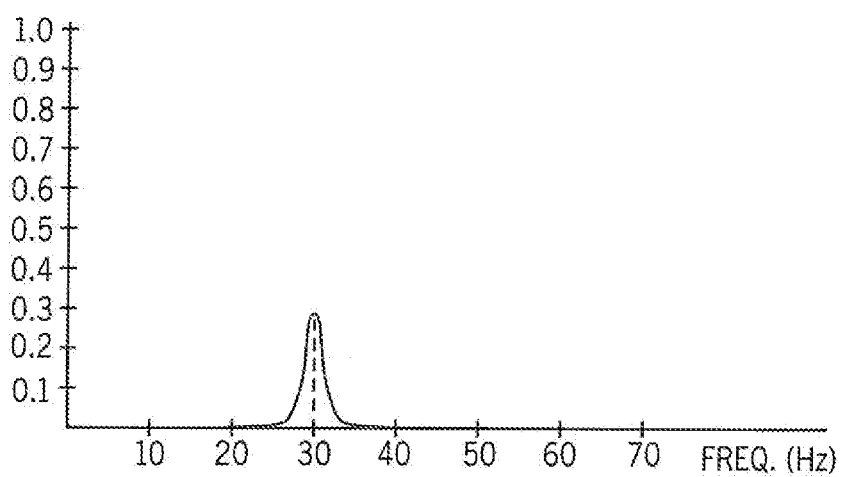
FIG. 9 is a graphical representation of a frequency response determined by one embodiment of a frequency transform utilized by the present invention.

When the motor 40 is operating, the motor drive 10 reads the expected frequency 242 and the corresponding threshold 244 from the memory device 45. Each of the expected frequencies 242 and corresponding thresholds 244 are provided as inputs to the condition monitor module 70. The DFT module 234 uses the expected frequencies 242 to determine a frequency response 236 of the estimated torque signal at each of the expected frequencies 242. An exemplary frequency response is illustrated in FIG. 9. The frequency response shows a vibration component present in the estimated torque signal at 30 Hertz with an amplitude of about thirty percent of rated torque. The logic circuit 240 receives both the expected frequency 242 and the corresponding threshold 244 as inputs and, if one of the expected frequencies is 30 Hertz, the logic circuit 240 will determine whether the magnitude of the vibration component exceeds the threshold 244 for 30 Hertz. If, for example, the threshold 244 for 30 Hertz is set to twenty percent for the exemplary frequency response, the logic circuit 240 will set a status flag 250 indicating that excessive vibration is present at the predefined frequency. If, however, the threshold 244 for 30 Hertz were set to forty percent, the logic circuit 240 would clear the status flag 250 for the predefined frequency.

As indicated above, certain conditions may exhibit vibrations at multiple frequencies. The logic circuit 240 may include a table storing different combinations of frequencies and the corresponding condition indicated by each combination of frequencies. The logic circuit 240 may compare the magnitudes of multiple frequency components in the frequency response to multiple corresponding thresholds. For example, the table may store a first threshold for a magnitude of vibration in the torque estimate at one times the angular velocity of the motor, a second threshold for a magnitude of vibration in the torque estimate at two times the angular velocity of the motor, and a third threshold for a magnitude of vibration in the torque estimate at two times the angular velocity of the motor, where the three thresholds are set to expected levels of vibration that would occur when there is angular misalignment between the motor shaft and the driven mechanical system. When monitoring the condition of the mechanical system driven by the motor 40, if the logic circuit 240 identifies that the magnitude of vibration at all three frequencies exceeds the preset thresholds, a status flag 250 may be set indicating the angular misalignment.

It is further contemplated that the status flags 250 may be transmitted to an external device from the motor drive 10. According to one embodiment, an output signal may be defined on the motor drive 10 that corresponds to one of the status flags 250. A discrete logic signal may then be transmitted, for example, to an input module on a programmable logic controller (PLC) from the motor drive 10 corresponding to the condition of the status flag 250. Optionally, the status flag 250 may be included as a bit or within a data word of a network packet, and the motor drive 10 may transmit the network packet to another device, such as a (PLC), industrial computer, or other such device monitoring the status of the motor drive 10, thereby providing the monitoring device information corresponding to the condition of the status flag 250. Further, multiple status flags 250 may be defined for separate frequencies and each status flag 250 set or reset independently of the other according to the magnitude of vibration present at the corresponding frequency.

It should be understood that the invention is not limited in its application to the details of construction and arrangements of the components set forth herein. The invention is capable of other embodiments and of being practiced or carried out in various ways. Variations and modifications of the foregoing are within the scope of the present invention. It also being understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention.

We claim:

1. A method for monitoring vibration in a motor connected to a motor drive, the method comprising the steps of:
    receiving a reference signal at a controller in the motor drive, wherein the reference signal corresponds to a desired operation of the motor connected to the motor drive;
    receiving a feedback signal at the controller from a position feedback device operatively connected to the motor;
    generating a torque reference signal with the controller, wherein the torque reference signal is a function of the reference signal and of the feedback signal;
    determining an estimated torque signal in a condition monitor module executing on the controller, wherein the estimated torque signal is a function of the feedback signal and of the torque reference signal;
    generating a frequency response of the estimated torque signal with the controller, wherein the frequency response includes a plurality of frequencies and a plurality of magnitudes identified within the estimated torque signal and wherein each magnitude in the plurality of magnitudes corresponds to one frequency in the plurality of frequencies;
    reading at least one frequency and at least one threshold into the controller from a memory device in the motor drive, wherein the memory device includes non-transitory memory and each of the at least one thresholds corresponds to one of the at least one frequencies;

setting a status flag on the motor drive when the magnitude of the frequency in the frequency response is greater than the threshold of the corresponding frequency stored in the non-transitory memory; and resetting the status flag on the motor drive when the magnitude of the frequency in the frequency response is less than the threshold of the corresponding frequency stored in the non-transitory memory.

2. The method of claim 1 further comprising the step of determining one of an angular position, an angular velocity, and an angular acceleration from the feedback signal received at the controller from the position feedback device and wherein the estimated torque signal is a function of one of the angular position, the angular velocity, and the angular acceleration determined from the feedback signal.

3. The method of claim 1 further comprising an initial step of storing each of the at least one frequencies and the corresponding threshold in the non-transitory memory wherein each frequency stored corresponds to an expected frequency of a vibration present in the motor.

4. The method of claim 3, the method further comprising the steps of:
measuring an angular velocity at which the motor is operating as a function of the feedback signal; and
determining the expected frequency as a function of the angular velocity.

5. The method of claim 1 wherein the step of generating the frequency response further comprises the steps of:
storing a plurality of samples of the estimated torque signal in the memory device in the motor drive; and
inputting the plurality of samples into a discrete Fourier transform module.

6. The method of claim 5 wherein each of the at least one frequencies read from the non-transitory memory is provided as an input to the discrete Fourier transform module and wherein the frequency response includes a frequency corresponding to each of the at least one frequencies.

7. A motor drive operative to determine a vibration in a motor connected to the motor drive, the motor drive comprising:
a first input configured to receive a reference signal corresponding to a desired operation of the motor connected to the motor drive;
a second input configured to receive a feedback signal from a position feedback device operatively connected to the motor;
a memory device configured to store a plurality of instructions, wherein the memory device includes non-transitory memory; and
a controller configured to execute the plurality of instructions to:
generate a torque reference signal as a function of the reference signal and of the feedback signal,
determine an estimated torque signal as a function of the feedback signal and of the torque reference signal;
generate a frequency response of the estimated torque signal, wherein the frequency response includes a plurality of frequencies and a plurality of magnitudes identified within the estimated torque signal and wherein each magnitude in the plurality of magnitudes corresponds to one frequency in the plurality of frequencies;
read at least one frequency and at least one threshold from the non-transitory memory, wherein each of the at least one thresholds corresponds to one of the at least one frequencies;

set a status flag on the motor drive when the magnitude of the frequency in the frequency response is greater than the threshold of the corresponding frequency stored in the non-transitory memory; and
reset the status flag on the motor drive when the magnitude of the frequency in the frequency response is less than the threshold of the corresponding frequency stored in the non-transitory memory.

8. The motor drive of claim 7 wherein the controller includes a logic circuit configured to:
receive the frequency response of the estimated torque signal as an input,
receive the at least one frequency and the at least one threshold as inputs, and
set and reset the status flag on the motor drive.

9. The motor drive of claim 7 wherein the controller is further configured to execute the plurality of instructions to determine one of an angular position, an angular velocity, and an angular acceleration from the feedback signal and wherein the estimated torque signal is a function of one of the angular position, the angular velocity, and the angular acceleration determined from the feedback signal.

10. The motor drive of claim 7 wherein the controller is further configured to generate the frequency response by:
storing a plurality of samples of the estimated torque signal in the memory device in the motor drive; and
inputting the plurality of samples into a discrete Fourier transform module.

11. The motor drive of claim 10 wherein each of the at least one frequencies read from the non-transitory memory is provided as an input to the discrete Fourier transform module and wherein the frequency response includes a frequency corresponding to each of the at least one frequencies.

12. The motor drive of claim 7 further comprising an output configured to transmit the status flag to a remote device.

13. A method for monitoring vibration in a motor connected to a motor drive, the method comprising the steps of:
determining an estimated torque present at an output of the motor using a controller executing in the motor drive;
generating a frequency response of the estimated torque using the controller executing in the motor drive, wherein the frequency response includes a plurality of frequencies and a plurality of magnitudes identified within the estimated torque and wherein each magnitude in the plurality of magnitudes corresponds to one frequency in the plurality of frequencies;
reading at least one frequency and at least one threshold into the controller from a memory device in the motor drive, wherein the memory device includes non-transitory memory and each of the at least one thresholds corresponds to one of the at least one frequencies;
setting a status flag on the motor drive when the magnitude of the frequency in the frequency response is greater than the threshold of the corresponding frequency stored in the non-transitory memory; and
resetting the status flag on the motor drive when the magnitude of the frequency in the frequency response is less than the threshold of the corresponding frequency stored in the non-transitory memory.

14. The method of claim 13 wherein the step of determining the estimated torque present at the output of the motor further comprises the steps of:
obtaining a position feedback signal from a position feedback device operatively connected to the motor;

generating a torque reference signal with the controller in the motor drive, wherein the torque reference signal corresponds to a desired operation of the motor connected the motor drive; and determining the estimated torque as a function of the position feedback signal and of the torque reference signal.

15. The method of claim 14 wherein the step of determining the estimated torque present at the output of the motor further comprises the step of determining one of an angular position, an angular velocity, and an angular acceleration from the position feedback signal, wherein the estimated torque is determined as a function of one of the angular position, the angular velocity, and the angular acceleration determined from the position feedback signal.

16. The method of claim 14 further comprising an initial step of storing each of the at least one frequencies and the corresponding threshold in the non-transitory memory wherein each frequency stored corresponds to an expected frequency of a vibration present in the motor.

17. The method of claim 16, the method further comprising the steps of:

measuring the angular velocity at which the motor is operating as a function of the position feedback signal; and determining the expected frequency as a function of the angular velocity.

18. The method of claim 13 wherein the step of generating the frequency response further comprises the steps of:

storing a plurality of samples of the estimated torque in the memory device in the motor drive; and inputting the plurality of samples into a discrete Fourier transform module.

19. The method of claim 18 wherein each of the at least one frequencies read in from the non-transitory memory is provided as an input to the discrete Fourier transform module and wherein the frequency response includes a frequency corresponding to each of the at least one frequencies.

20. The method of claim 13 further comprising the step of transmitting the status flag to a remote device.

* * * * *